(12) United States Patent
Sheridan et al.

(10) Patent No.: US 6,475,347 B1
(45) Date of Patent: Nov. 5, 2002

(54) HIGH BOILING INHIBITORS FOR DISTILLABLE, POLYMERIZABLE MONOMERS

(75) Inventors: Robert E. Sheridan, Marietta, OH (US); Kenneth W. Hartman, Middleburne, WV (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 09/924,276

(22) Filed: Aug. 8, 2001

(51) Int. Cl.$^7$ ............... B01D 3/00; C07F 7/08
(52) U.S. Cl. ............... 203/6; 203/7; 203/65; 544/170; 556/401; 558/194
(58) Field of Search ............ 556/401; 558/194; 544/170; 206/6, 7, 65

(56) References Cited

U.S. PATENT DOCUMENTS

| | | | |
|---|---|---|---|
| 3,258,477 A | 6/1966 | Plueddemann et al. | 260/448.8 |
| 4,709,067 A | 11/1987 | Chu et al. | 556/440 |
| 4,780,555 A | 10/1988 | Bank | 556/440 |
| 4,946,977 A | 8/1990 | Bernhardt et al. | 556/440 |
| 5,103,032 A | 4/1992 | Turner et al. | 556/401 |
| 5,145,979 A | 9/1992 | Takatsuna et al. | 556/440 |
| 5,616,753 A | 4/1997 | Turner et al. | 556/401 |
| 5,723,643 A | 3/1998 | Mikami et al. | 556/440 |
| 5,914,418 A | 6/1999 | Mikami et al. | 556/401 |

Primary Examiner—Joseph K. McKane
Assistant Examiner—Kamal Saeed
(74) Attorney, Agent, or Firm—Michael P. Dilworth

(57) ABSTRACT

Disclosed herein are compounds of the structure

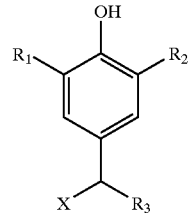

wherein $R_1$, $R_2$, and $R_3$ are organic radicals of $C_1$ to $C_{20}$, such that the combination of the three contain at least twelve carbon atoms and $R_3$ is bound to the methylene carbon atom between X and the aromatic ring by at least one saturated carbon atom, allowing it to be easily separated from the polymerizable monomer by distillation;

$R_1$ and $R_2$ have sufficient steric bulk to protect the phenol from reacting with an alkoxy group or halogen bound to silicon; and X is a neutral heteroatomic radical of oxygen, nitrogen, or phosphorus; and their use as inhibitors for the polymerization of (meth)acryloxysilanes.

6 Claims, No Drawings

HIGH BOILING INHIBITORS FOR DISTILLABLE, POLYMERIZABLE MONOMERS

BACKGROUND OF THE INVENTION

1. Field of Invention

The present invention relates to polymerization inhibitors for use in the stabilization of polymerizable monomers, compositions containing them, and their preparation. More particularly, this invention is directed to the use of these inhibitors as stabilizers during the production and subsequent storage of acryloxysilanes and methacryloxysilanes.

2. Description of Related Art

Acryloxysilanes and methacryloxysilanes are chemically reactive materials that are useful in many commercial applications. For example, such compounds are useful as coupling agents to bond organic compounds to inorganic materials. In particular, 3-methacryloxypropyltrimethoxysilane is widely used as a coupling agent in enhancing the performance of fiberglass-reinforced products.

U.S. Pat. No. 3,258,477 discloses silanes characterized by a trifunctional silicon atom at one end of the molecule and an acryloxy group on the other end of the molecule and to aqueous solutions formed therefrom.

U.S. Pat. No. 3,305,483 discloses a method of preparation and compositions of a variety of hindered phenolic benzylamines, which are antioxidants, wherein the linkage between benzylic nitrogen and aromatic rings is limited to a methylene group.

U.S. Pat. No. 4,709,067 discloses a process for preparing, purifying and/or storing methacryloxy or acryloxy containing organosilicon compounds without the undesirable polymerization normally associated with the methacrylate bonds. In an alternative embodiment, the process includes the addition of certain stabilizers, and in particular diketone or ketoester stabilizers.

U.S. Pat. No. 4,780,555 discloses a method for preparing acryl-functional halosilanes by reacting a halosilane with an acryloxy or methacryloxy-functional organic compound in the presence of a platinum hydrosilation catalyst and a stabilizing amount of phenothiazine, wherein the reaction mixture is contacted with an oxygen-containing inert gas. A method for stabilizing the above reaction mixture by contacting it with the oxygen-containing gas is also disclosed.

U.S. Pat. No. 5,103,032 discloses compositions containing an acryloxysilane or a methacryloxysilane and an N,N-dialkylaminomethylene phenol in an amount at least sufficient to inhibit polymerization of the silane during its formation, purification, and storage. Methods for producing such compositions are also provided.

U.S. Pat. No. 5,145,979 discloses processes for the preparation of γ-methacryloxypropylsilane compounds which comprise carrying out the reaction of allyl methacrylate with a hydrosilane compound in the presence of a platinum catalyst, while allowing at least one of a hindered phenol compound and an aromatic amine compound to coexist in the reaction system with an alkylamine compound or an amide compound, or with a gas containing molecular oxygen, or with a phenol compound having an aminoalkylene group. By using these processes as provided, gelation of the reaction mixture in the reaction system and during the course of purification thereof by distillation is said to be effectively avoided and the desired γ-methacryloxypropylsilane compounds obtained in good yield.

U.S. Pat. No. 5,616,753 discloses a method for inhibiting the polymerization of unsaturated silanes by the addition of a non-aromatic stable free radical during any of the steps of the formation of the desired silane, the purification of the desired silane, and to the desired silanes, as well as compositions of the inhibitors and the silanes. Particular classes of silanes to be inhibited include acryloxy-, methacryloxy-, and vinyl-functional silanes. The free radicals for use as inhibitors include various nitroxides. The free radicals are effective as inhibitors at elevated temperatures, for extended periods of time, and even in the absence of molecular oxygen.

U.S. Pat. No. 5,616,774 and commonly assigned E. P. No. 744,392 disclose hindered phenolic benzylamines wherein the methylene linkages between benzylic nitrogen and aromatic rings are substituted with aromatic or otherwise multiply bonded carbon groups or heteroatom groups, wherein said amines are isolated or non-isolated intermediates leading to the ultimate preparation of stable hindered quinone methides.

U.S. Pat. No. 5,723,643 discloses a method to make high-purity acryloxy- or methacryloxy-functional organosilicon compounds in high yields by inhibiting gelation of the reaction product during preparation. The method comprises (A) reacting an acrylate or methacrylate ester of an alcohol comprising an aliphatically unsaturated bond or a phenol comprising an aliphatically unsaturated bond with a (B) SiH-functional silicon compound in the presence of (C) a hydrosilylation reaction catalyst and (D) a polymerization inhibitor described by a given formula. The method can further comprise distillation of the reaction mixture resulting from the reaction of component (A) and (B) in the presence of component (D).

U.S. Pat. No. 5,914,418 discloses a method for inhibiting polymerization of acrylic-functional silanes comprising forming a mixture comprising an acrylic-functional silane and a polymerization inhibitor described by a given formula.

The disclosures of the foregoing are incorporated herein by reference in their entirety.

SUMMARY OF THE INVENTION

This invention relates to the composition and method of preparation of polymerization inhibitors and compositions containing them for use in the stabilization of polymerizable monomers. Furthermore, this invention encompasses the use of these inhibitors as stabilizers during the production and storage of acryloxysilanes and methacryloxysilanes. (For convenience, the term "(meth)acryloxysilanes" will be used hereinafter to refer to both acryloxysilanes and methacryloxysilanes.) The inhibitors described herein and potential degradation products thereof can be easily removed from the (meth)acryloxysilane monomers by distillation, thus allowing for them to be easily substituted by a second polymerization inhibitor with more desirable physical properties.

More specifically, the present invention is directed to a compound of the structure

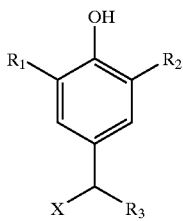

wherein $R_1$, $R_2$, and $R_3$ are organic radicals of $C_1$ to $C_{20}$, such that the combination of the three contain at least twelve carbon atoms and $R_3$ is bound to the methylene carbon atom between X and the aromatic ring by at least one saturated carbon atom, allowing it to be easily separated from the polymerizable monomer by distillation;

$R_1$ and $R_2$ have sufficient steric bulk to protect the phenol from reacting with an alkoxy group or halogen bound to silicon; and X is a neutral heteroatomic radical of oxygen, nitrogen, or phosphorus.

In another aspect, the present invention is directed to a composition comprising a (meth)acryloxysilane and a stabilizing amount of at least one compound of the structure

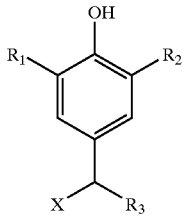

wherein $R_1$, $R_2$, and $R_3$ are organic radicals of $C_1$ to $C_{20}$, such that the combination of the three contain at least twelve carbon atoms and $R_3$ is bound to the methylene carbon atom between X and the aromatic ring by at least one saturated carbon atom, allowing it to be easily separated from the polymerizable monomer by distillation;

$R_1$ and $R_2$ have sufficient steric bulk to protect the phenol from reacting with an alkoxy group or halogen bound to silicon; and X is a neutral heteroatomic radical of oxygen, nitrogen, or phosphorus.

In still another aspect, the present invention is directed to a method for the stabilization of (meth)acryloxysilanes during their production, storage, or both comprising adding thereto a compound of the structure

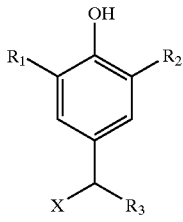

wherein $R_1$, $R_2$, and $R_3$ are organic radicals of $C_1$ to $C_{20}$, such that the combination of the three contain at least twelve carbon atoms and $R_3$ is bound to the methylene carbon atom between X and the aromatic ring by at least one saturated carbon atom, allowing it to be easily separated from the polymerizable monomer by distillation;

$R_1$ and $R_2$ have sufficient steric bulk to protect the phenol from reacting with an alkoxy group or halogen bound to silicon; and X is a neutral hetero atomic radical of oxygen, nitrogen, or phosphorus.

DESCRIPTION OF THE PREFERRED EMBODIMENTS (Meth)acryloxysilanes can be prepared by the known reaction between organosilicon compounds having an Si—H function group and acryloxy and methacryloxy compounds having additional aliphatic unsaturation, as has been described, for example, by Plueddemann and Clark in U.S. Pat. No. 3,258,477 and by Chu and Kanner in U.S. Pat. No. 4,709,067. For example, 3-methacryloxypropyltrimethoxysilane (MAOP-TMS) can be prepared by the known reaction of allyl methacrylate with trimethoxysilane, as shown in the following equation (1):

$$CH_2\!=\!C(CH_3)C(O)OCH_2CH\!=\!CH_2 + (CH_3O)_3Si\!-\!H \rightarrow$$
$$CH_2\!=\!C(CH_3)C(O)OCH_2CH_2CH_2\!-\!Si(OCH_3)_3 \text{ MAOP-TMS} \quad (1)$$

Likewise, reaction of allyl methacrylate with trichlorosilane, $Cl_3Si$—H, provides 3-methacryloxypropyltrichlorosilane, which, in turn, can be reacted with methanol to produce MAOP-TMS. When allyl acrylate is used in place of allyl methacrylate, the corresponding acryloxypropyltrimethoxy-(or trichloro-)silanes are provided. Owing to the exothermic nature of such hydrosilation reactions and the presence of catalytic platinum-hydrosilane complexes, polymerization of the highly reactive acryloxysilane and methacryloxysilane product can occur as product is formed. Such polymerization can also be induced during esterification of the trichlorosilane intermediate to the corresponding trialkoxysilane product, such as, for example, during reaction of the aforementioned 3-methacryloxypropyltrichlorosilane with methanol to produce MAOP-TMS.

Undesirable polymerization can also occur during purification of the crude reaction product. Typically, purification is accomplished by distillation, which is preferably carried out at as low a temperature as is feasible to minimize polymerization. Even purified product may tend to polymerize during storage prior to end use. Depending on the extent of such polymerization during initial formation, purification, and storage of acryloxy- and methacryloxysilanes, thickening, and even gelling, may occur, resulting in increased maintenance to remove the thickened or gelled material from equipment or in unsalable product.

In U.S. Pat. No. 5,103,032, Turner et al. describe the use of N,N-dialkylaminomethylene phenols as polymerization inhibitors for acryloxy- and methacryloxy silanes during their formation, purification, and storage. Similarly, in U.S. Pat. No. 5,145,979, Takatsuna et al. describe the use of similar compounds for the same purpose.

It has been found that, during the course of the hydrosilation reaction, this inhibitor gradually breaks down to form 2,6-di-t-butylcresol (also referred to as BHT or Ionol). In the case of the commercially important MAOP-TMS, this butylated cresol is known to co-distill with the product. This hurts the end use of this material in certain applications by imparting an undesirable water insolubility characteristic to the final product.

Inhibitor Composition

The inhibitors of the present invention are substituted phenols of the formula

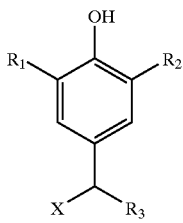

wherein $R_1$, $R_2$, and $R_3$ are organic radicals of $C_1$ to $C_{20}$, such that the combination of the three impart sufficient mass to the molecule to allow it and its potential degradation products to be easily separated from the polymerizable monomer by distillation. The potential degradation products are XH, with X as defined above, and the substituted phenol above wherein X is replaced by hydrogen. The volatilities, i.e., boiling points of XH and the phenolic degradation product are preferably selected such that XH has a boiling point below the silane product, and the phenolic degradation product has a boiling point above the silane product. Alternatively, both potential degradation products can be selected with boiling points above that of the silane product. The difference in boiling point, above or below that of the silane product, is preferably at least 20° C. at the desired distillation pressure. For MAOP-TMS, this is preferably accomplished when $R_1$, $R_2$, and $R_3$ total at least twelve carbon atoms and $R_3$ is bound to the methylene carbon atom between X and the aromatic ring by at least one saturated carbon atom. X is a neutral heteroatomic radical of oxygen, nitrogen, or phosphorus and is selected from a broad range of oxygen, nitrogen, and phosphorus-bound radicals, including esters, ethers, amines, imines, phosphines, phosphates, and the like, with amines, carbon esters, silyl ethers, and phosphines being preferred. The morpholino group is a particularly preferred embodiment of X. Furthermore, $R_1$ and $R_2$ should have sufficient steric bulk so as to protect the phenol from reacting with an alkoxy group or halogen bound to silicon, for example, t-butyl, iso-octyl, t-amyl, t-hexyl, s-butyl, s-amyl, and the like.

Specific examples of such compounds include:

2,6-di-tert-butyl-4-(1-dimethylamino-3-phenylpropyl) phenol,
2,6-di-tert-butyl-4-(1-morpholino-3-phenylpropyl)phenol,
2,6-di-tert-butyl-4-(1-trimethylsilyloxy-3-phenylpropyl) phenol,
2,6-di-tert-butyl-4-(1-triphenylsilyloxy-3-phenylpropyl) phenol,
2,6-di-tert-butyl-4-(1-diphenylmethylsilyloxy-3-phenylpropyl)phenol,
2,6-di-tert-butyl-4-(1-tri-iso-propylsilyloxy-3-phenylpropyl)phenol,
2,6-di-tert-butyl-4-(1-diphenylphospho-3-phenylpropyl) phenol,
2,6-di-tert-butyl-4-(1-benzoyl-3-phenylpropyl)phenol,
2,6-di-tert-butyl-4-(1-dimethylaminotridecyl)phenol,
2,6-di-tert-butyl-4-(1-morpholinotridecyl)phenol,
2,6-di-tert-butyl-4-(1-trimethylsilyloxytridecyl)phenol,
2,6-di-tert-butyl-4-(1-diphenylphosphotridecyl)phenol,
2,6-di-tert-butyl-4-(1-benzoyltridecyl)phenol,
2,6-di-t-butyl-4-(1-benzoylpentyl)phenol,
2,6-di-t-butyl-4-(morpholinopentyl)phenol,
2,6-di-t-butyl-4-(1-dimethylaminopentyl)phenol, and
2,6-di-isooctyl-4-(1-dimethylamino-3-phenylpropyl) phenol.

Inhibitor Synthesis

The inhibitors described above can be made by the use of standard organic reactions. For example, the Grignard reaction between phenethylmagnesium chloride and 3,5-di-t-butyl-4-hydroxybenzaldehyde produces 2,6-di-t-butyl-4-(1-hydroxy-3-phenylpropyl)phenol. This alcohol can be silylated by known techniques with the corresponding chlorosilane to yield the "silyloxy" derivatives listed above. Further treatment of the trimethylsilyloxy derivative with an amine, such as morpholine or dimethylamine, produces the amine derivatives described.

Treatment of the product alcohol from the Grignard reaction with chlorophosphines yields the phosphinite derivatives. Similarly, the organic esters can be made by reacting the same alcohol with the corresponding acid chloride or anhydride. Many synthetic variations will lead to the desired inhibitors.

The present invention also encompasses the use of such inhibitors and inhibitor-containing compositions in the production of (meth)acryloxysilanes. It further encompasses the separation of the inhibitor from the (meth)acryloxysilane and its substitution by a second polymerization inhibitor having more desirable physical properties, such as water solubility.

In the (meth)acryloxysilanes that are stabilized with the above described phenolic inhibitors, the (meth)acryloxy moieties are bonded to silicon through an alkylene or alkyleneoxy bridge and the silicon is further bonded to alkoxy groups or halides. Preferably, the silanes are those encompassed by the general formula A shown below:

General Formula A

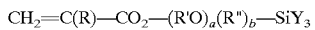

wherein:
  R is hydrogen or methyl;
  R' is alkylene of two to four carbon atoms;
  R" is alkylene, preferably of from one to four carbon atoms;
  Y is halide, alkoxy, or alkoxy-substituted alkoxy groups, wherein the alkoxy preferably has from one to four carbon atoms, or an alkyl group, preferably of from one to four carbon atoms;
  a is zero to ten, preferably zero to five;
  b is at least one; and
  a+b is a number from one to eleven, preferably one to six.

The R' and R" groups can be linear or branched, and any combination of such groups can be present. The divalent R' group is exemplified by ethylene (—$CH_2CH_2$—) and higher homologous groups, such as propylene, isopropylene, butylene, and the like. R" can be any such alkylene groups and, in addition, can be methylene.

The Si-bonded Y groups are preferably any $C_1$–$C_4$ linear or branched alkoxy groups (e.g., methoxy, ethoxy, isopropoxy, and the like) or $C_1$–$C_4$ alkoxy-substituted $C_1$–$C_4$ alkoxy groups (e.g., β-methoxyethoxy), or halides, such as, in particular, chlorine and bromine.

Illustrative of such (meth)acryloxysilanes that can be stabilized as described herein are:
3-acryloxypropyltrimethoxysilane,
3-acryloxypropyltriethoxysilane, 3-acryloxypropylmethyldimethoxysilane,
3-acryloxypropylmethyldiethoxysilane,
3-acryloxypropyldimethylmethoxysilane,
3-acryloxypropyldimethylethoxysilane,
3-methacryloxypropyltrimethoxysilane,
3-methacryloxyisobutyltrimethoxysilane,3-methacryloxypropylmethyldimethoxysilane,
3-methacryloxypropylmethyldiethoxysilane,
3-methacryloxypropyldimethylmethoxysilane,
3-methacryloxypropyldimethylethoxysilane,
3-methacryloxyisobutylmethyldimethoxysilane,
3-methacryloxypropyltriethoxysilane,
3-acryloxypropyltrichlorosilane,
3-methacryloxypropyltrimethylsilane,
3-methacryloxypropyltrichlorosilane,
3-methacryloxyisobutyltrichlorosilane,
3-methacryloxypropyl[tris(beta-methoxyethoxy)]silane, and the like.

The above-described (meth)acryloxysilanes are prepared by methods known in the art, such as those described in the aforementioned U.S. Pat. Nos. 3,258,477 and 4,709,067, which are incorporated herein by reference. For example, (meth)acryloxysilanes encompassed by general formula A above can be prepared by the reaction of an SiH functional compound and an ester of acrylic or methacrylic acid wherein the ester moiety has an ethylenically unsaturated group, as shown by the following equation (1):

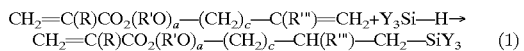

$$CH_2=C(R)CO_2(R'O)_a-(CH_2)_c-C(R''')=CH_2+Y_3Si-H \rightarrow$$
$$CH_2=C(R)CO_2(R'O)_a-(CH_2)_c-CH(R''')-CH_2-SiY_3 \quad (1)$$

where: R, R', a, and Y are as defined above with respect to general formula A; R''' is hydrogen or methyl; and c is zero or one; and the $-(CH_2)_c-CH(R''')CH_2-$ group is illustrative of the R'' alkylene group of general formula A. The hydrosilation reactions encompassed by equation (1) are normally effected at a temperature from about 70° C. to about 120° C. in the presence of a platinum-containing catalyst, such as those described in U.S. Pat. No. 4,709,067. The platinum-containing hydrosilation catalyst may be chosen from the group of supported platinum-catalysts, such as platinum on γ-alumina or on charcoal, or from the group of homogeneous soluble platinum complexes, such as chloroplatinic acid bis-(ethylene platinous)chloride, dichlorobis (acetonitrile)platinum (II), cis-dichlorobis (triphenylphosphine)platinum (II), tetrakis (triphenylphosphine)platinum (O) or other soluble platinum complexes well known in the art. The soluble platinum complexes are normally in solution in solvents such as isopropanol, acetonitrile, or 1,2-dimethoxyethane. The concentration of the platinum catalyst required depends on reaction temperature and time, but is generally used in the range of from about 2 to about 100 ppm and preferably from about 10 to about 25 ppm, based on the total weight of the hydrosilane and allyl methacrylate.

With reference to the hydrosilation reaction of equation (1), it is to be understood that when the desired product is a (meth)acryloxytrialkoxysilane (i.e., when Y of general formula A is an alkoxy group), the Y group of the H—SiY$_3$ reactant of equation (1) can be halogen, preferably chlorine, or alkoxy. When Y of the reactant is chlorine, for example, the product of equation (1) is the corresponding trichlorosilane, which can then be esterified with an alcohol, such as methanol, by methods known in the art to provide the desired trialkoxysilane.

Alternatively, the desired trialkoxysilane can be produced directly by the hydrosilation reaction of equation (1) by the use of a trialkoxysilane reactant, H—SiY$_3$, in which Y is alkoxy. Y may also be an alkyl group, preferably of from one to four carbon atoms, more preferably a methyl group, such that the corresponding silanes with two, one, or even no hydrolyzable groups are encompassed by the present invention. It is to be understood, therefore, that the inhibitors used in the present invention can be provided to the reaction mixture that produces the desired product directly, or to an intermediate reaction mixture.

In addition to hydrosilation, the (meth)acryloxysilanes that are stabilized as described herein can be prepared by the reaction of a tertiary amine or alkali metal salt of acrylic or methacrylic acid with a chloroalkylsilane as described in U.S. Pat. Nos. 3,258,477 and 4,946,977. This chloroalkylsilane is of the formula:

$$ClCH_2(CH_2)_xSi(R^1)_3$$

wherein $R^1$ is an alkoxy or acyloxy radical and x is 0, 1, 2, or 3. Triethylamine is a preferred amine to form the reactant salt, and the salt as such does not necessarily have to be isolated. Thus, the amine, or alkali metal base, and the chosen acid can simply be mixed, and the chloroalkylsilane added to the mixture in approximately stoichiometric quantities. The reaction is preferably carried out in the presence of an inert organic solvent, such as benzene, toluene, xylene, or cyclohexane, at reaction temperatures of about 100° C. to about 150° C.

In accordance with one embodiment of the process of the present invention, the inhibitor is provided to the reaction mixture used to produce the (meth)acryloxysilane to be stabilized. Such (meth)acryloxysilane-forming reaction mixtures include those containing the above-described hydrosilation reactants (e.g., an ethylenically unsaturated ester of acrylic or methacrylic acid and an SiH functional compound, such as a trialkoxysilane or trihalosilane), as well as mixtures containing a tertiary amine salt or an alkali metal salt of acrylic or methacrylic acid and a chlorosilane (e.g., chloromethyltrimethoxysilane and chloropropyltrimethoxysilane).

In accordance with another embodiment of the present invention, the inhibitor is provided to the (meth) acryloxysilane-containing mixture to be purified by distillation.

The inhibitor may be provided by adding it as a separate stream directly to the zone in which the (meth) acryloxysilane is either to be formed initially or purified. Alternatively, the inhibitor can be provided to the zone as a component of one or more reactant streams, or as a component of the mixture to be distilled. The inhibitor can also be provided to the recovered or final product, such as prior to packaging, storage, or shipping. Preferably, it is added just prior to the process steps requiring inhibition, more preferably using multiple additions of the inhibitor during the overall manufacturing process (initial reaction, purification, and recovery of product). It is to be understood that the inhibitor can be provided at any step of a batch or continuous process for (meth)acryloxysilane manufacture, without departing from the scope of this invention.

The stabilization of (meth)acryloxysilanes is effected by employing the inhibitor in an amount at least sufficient to prohibit polymerization. The particular minimal amount used depends largely on the severity of the conditions to which the silane will be subjected during its initial formation, purification, and storage. For example, in general, the higher the temperature the more susceptible the silane will be to polymerization. Further, the lower the free oxygen content to which the silane or silane-containing medium is exposed, the greater the tendency of the silane to polymerize. Some oxygen in the vapor space above the (meth)acryloxysilane is beneficial in inhibiting polymerization; however, as the concentration of oxygen in the vapor space increases, the level of dissolved oxygen in the silane-containing medium also increases. High levels of dissolved oxygen within the (meth)acryloxysilane-containing medium can lead to peroxide formation, which, in turn, can initiate polymerization. Thus, subjecting the silane or silane-containing medium to high temperatures, and/or to oxygen levels that promote peroxide formation, substantially increases the minimum effective amount of inhibitor.

In addition to oxygen level and temperature, other conditions that can induce polymerization of (meth) acryloxysilanes are metal contaminants, ultraviolet light, and free radical initiators. Illustrative of the latter are oxygen-derived peroxy and peroxide, as well as alkoxy, aryloxy, alkyl, and aryl free radicals.

Generally, oxygen levels of approximately 0.1 to 4 percent by volume in nitrogen are believed to be beneficial in aiding inhibitors in inhibiting polymerization; see U.S. Pat. No. 4,780,555. However, with increasing levels of dissolved oxygen, peroxide radicals can form to an extent sufficient to initiate polymerization, as noted above, despite the presence of inhibitors. In order to minimize free radical formation, oxygen levels should not exceed percent by volume of the vapor space throughout the (meth)acryloxysilane-forming reaction and purification process.

Generally, about 5 to 2,000 ppm (parts by weight per million parts by weight of silane) of the inhibitor are sufficient to prevent polymerization of (meth) acryloxysilanes. Normally, no more than about 100 to 500 ppm are required. It is to be understood, however, that exposure of the (meth)acryloxysilanes to severe conditions will require correspondingly higher levels of inhibitor, such as about 1,000 ppm or more. For example, high temperature distillation (160° to 190° C.) or exposure to a combination of conditions that accelerate polymerization, such as exposure to atmospheric conditions (21 percent oxygen by volume) and heat (e.g., 140° C.) will result in gelling of (meth)acryloxysilanes unless substantially higher inhibitor levels are used, such as about 1,000 to 2,500 ppm of inhibitor being present during the (meth)acryloxysilane-forming reaction, with an additional 10 to about 325 ppm of inhibitor provided during distillation. A final addition of inhibitor can be added to the product in order to stabilize it during storage and distribution, the preferred range for this purpose being from about 5 to about 25 ppm.

Included in the scope of the present invention is the use of the phenolic inhibitors described in combination with other polymerization inhibitors, including those containing phenolic (—OH), amino (—NH), quinone (O=C), and nitroxide (N—O) functionality. Illustrative of such other inhibitors are: hydroquinone; benzoquinone; the monomethyl ether of hydroquinone (MEHQ); N,N'-diphenyl-p-phenylenediamine; phenothiazine; Ionol™; Isonox™ 129; Ethanox™ 702; Ethanox™ 703; Ethanox™ 330; 2,2,6,6-tetramethyl-1-piperidinyloxy free radical (TEMPO); 4-hydroxy TEMPO; and mixtures of the foregoing. The phenolic inhibitor of this invention is present in such combinations in an amount sufficient to provide a polymerization inhibitor system having improved performance relative to said other inhibitors or mixtures of said other inhibitors not containing the phenolic inhibitors of this invention.

The inhibitor is typically provided to the (meth) acryloxysilane-forming reaction and purification process as a solution. This technique provides more uniform dispersion of the inhibitor throughout the medium to be stabilized. Any solvent for the phenolic inhibitors of this invention may be used provided it does not adversely affect product quality or process control. Typically, the solvents selected are aromatic hydrocarbons well known in the art, such as toluene, benzene, xylene and the like, with toluene being preferred.

While the phenolic inhibitors of the present invention are surprisingly good at inhibiting the (meth)acryloxysilane polymerization during the hydrosilylation reaction, when used in higher concentrations they can be detrimental to the physical properties of the product. High concentrations of hindered phenolic inhibitors have a detrimental effect on, for example, the water solubility characteristics of the product. It is in accordance with this invention that these inhibitors can be easily separated from the (meth)acryloxysilane by distillation. This provides an opportunity to replace the phenolic inhibitor with a different inhibitor or combination of inhibitors that may impart more desirable properties to the final (meth)acryloxysilane than the phenolic inhibitor. Such inhibitors may include MEHQ or any of the nitroxyl based inhibitors such as TEMPO or 4-hydroxy-TEMPO described by Turner et at. in U.S. Pat. No. 5,616,753, which patent is incorporated herein by reference. In particular, the broader class of polymerizable silanes disclosed by Turner et al. can be inhibited by the inhibitors of the present invention.

Because the phenolic inhibitors described in this invention are typically higher boiling than the (meth) acryloxysilane, the second inhibitor needs to be added prior to or during the distillation to protect the lower boiling methacrylates which come overhead during the distillation. These lower boiling methacrylates, which must be removed, are unreacted allyl methacrylate and isomers thereof from the hydrosilation reaction. There are a number of ways to achieve this outcome known in the art. For example, the lower boiling inhibitor can be added to the (meth) acryloxysilane prior to distillation. In this case, the boiling point of the lower boiling inhibitor must be such that it co-distills with the methacrylate so that it protects it during all phases of the distillation. Alternatively, the lower boiling inhibitor can be continuously added to the (meth) acryloxysilane feed, to the base of the column or to other feed points in the column. An inhibitor that boils higher than the methacrylate could be added to the top of the distillation column so that it runs counter current to the methacrylate flow. In this last case, however, it may be required that a polymerization inhibitor also be placed into the vessel to which the stripped methacrylate is to be collected. It can also be envisioned that the lower boiling inhibitor can be injected anywhere along the distillation train to protect different segments from polymerization.

The advantages and the important features of the present invention will be more apparent from the following examples. All parts and percentages are by weight unless otherwise specified.

EXAMPLES

Example 1

The procedure used to determine gel time in the examples is as follows:

A thermocouple is used to measure the temperature of the (meth)acryloxysilane sample to be tested. The sample to be tested and a clean Teflon-covered magnetic stir bar are placed in a clean, dry 50 mL vial and sealed. The sample is purged with nitrogen at a rate of 200 cc per minute for 30 minutes to remove oxygen. A thermocouple is placed into the sample and the sample is heated to 140° C. in a constant temperature bath. When polymerization begins to occur the viscosity of the sample rises and a temperature gradient is observed. Eventually, with increasing polymerization, the temperature of the (meth)acryloxysilane sample will register as a temperature differential compared to the constant temperature bath. For purposes of the examples, a sample is considered to have gelled when the temperature within the sample deviates by approximately 2° C. from the constant temperature bath and stirring stops.

The results of this test for various compounds are listed in Table 1. Entries 1 to 4 are listed for comparison with some lower boiling analogs. Entry 4 was prepared by silylation of the corresponding alcohol with trimethylchlorosilane. These are comparative examples, which are outside the scope of the present invention. The entries 5 to 11 are examples of the inhibitors with higher boiling points as described herein.

TABLE 1

| Entry No. | Compound | 140° C. Stability (hours) |
|---|---|---|
| 1 | 2,6-di-t-butyl-4-methylphenol (BHT) | <1 |
| 2 | 2,6-di-t-butyl-4-dimethylaminomethylphenol (Ethanox 703) | 69 |
| 3 | 2,6-di-t-butyl-4-(morpholinomethyl)phenol | 94 |
| 4 | 2,6-di-t-butyl-4-(trimethylsilyloxymethyl)phenol | 85 |
| 5 | 2,6-di-t-butyl-4-(1-benzoylpentyl)phenol | 6 |
| 6 | 2,6-di-t-butyl-4-(morpholinopentyl)phenol | 18 |
| 7 | 2,6-di-t-butyl-4-(1-dimethylaminopentyl)phenol | 31 |
| 8 | 2,6-di-t-butyl-4-(1-dimethylamino-3-phenylpropyl)phenol | 16 |
| 9 | 2,6-di-t-butyl-4-(1-morpholino-3-phenylpropyl)phenol | 30 |
| 10 | 2,6-di-t-butyl-4-(1-morpholinotridecyl)phenol | 15 |
| 11 | 2,6-di-t-butyl-4-(1-dimethylaminotridecyl)phenol | 26 |

Example 2

This example demonstrates the use of these inhibitors under reaction conditions and their separation from the final reaction product by distillation.

(A) Inhibitor Use in the Synthesis of 3-methacryloxypropyltrimethoxysilane

To a two-liter round-bottom flask fitted with a mechanical stirrer, reflux condenser, thermometer, and a 3 percent $O_2/N_2$ sparge set for approximately 100 mL of gas per minute was fed a solution comprising 555.3 grams (4.41 moles) of allyl methacrylate (AMA), 1.05 grams (0.003 mole, 1891 ppm based on the weight of AMA) of 2,6-di-t-butyl-4-(1-morpholino-3-phenylpropyl)phenol, and 19 ppm platinum as chloroplatinic acid based on the weight of the AMA. This solution was added at approximately 4.9 mL/min for 10 minutes. During this time the pot contents were heated to 90° C. After 10 minutes, a second feed of trimethoxysilane (TMS) was started at a feed rate of approximately 4.3 mL/min. The two solutions were fed at these rates for two hours while maintaining a reaction temperature of 90° C. After two hours of feeding the solutions, the pot contents were held at 90° C. for an additional two hours. After this time the reaction was cooled. Gas chromatographic analysis of the crude mixture showed that the contents comprised 69.8 percent by weight of the desired product, 3-methacryloxypropyltrimethoxysilane, and 14.7 percent by weight of unreacted AMA and related isomers.

(B) Distillation of the Crude 3-methacryloxypropyltrimethoxysilane with Replacement of the 2,6-di-t-butyl-4-(1-morpholino-3-phenylpropyl) phenol with 4-methoxyphenol (MEHQ)

To a one-liter three-neck round-bottom flask were charged 458 grams of the crude 3-methacryloxypropyltrimethoxysilane made in part (A) of this example and two grams of 4-methoxyphenol (MEHQ). The flask was fitted with an addition funnel, thermometer, and a 10-tray adiabatic Oldershaw column on top of which was fitted a vacuum distillation head. The addition funnel was charged with a solution of two grams of 4-methoxyphenol dissolved in 20 grams of a high molecular weight polyalkylene glycol polyether. This solution was slowly added to the distillation pot throughout the distillation. After the low boiling components were removed three product cuts were taken. The product cuts were taken with temperatures in the distillation head between 95° and 98° C. and pressure of 0.5 to 1.0 mm Hg. A total of 306.4 grams of product was collected having an average purity of 97.8 percent. None of the 2,6-di-t-butyl-4-(1-morpholino-3-phenylpropyl)phenol was found in any of the product cuts. A 10 weight percent aliquot of this distilled product in water produced a clear aqueous solution.

Example 3

Synthesis of 2,6-di-t-butyl-4-(1-morpholino-3-phenylpropyl)phenol

This example describes the synthesis of one of the inhibitors described. All of the inhibitors described can be made by this procedure by appropriately substituting either the Grignard reagent, the chlorosilane, or the amine.

(A) 2,6-di-t-butyl-4-(1-hydroxy-3-phenylpropyl)phenol

To a 5-liter, 4-neck round-bottom flask fitted with a mechanical stirrer, reflux condenser, thermometer, and addition funnel were charged 238.5 grams (1.02 moles) of 3,5-di-t-butyl-4-hydroxybenzaldehyde and 979 grams of toluene. To this suspension, a one molar solution of phenethylmagnesium chloride in THF was slowly added such that the pot temperature slowly rose to 40° C. After the addition of several hundred milliliters of Grignard reagent solution a green sticky solid formed. The addition was halted, an additional 859 mL of toluene was added, and the solution was warmed to 80° C. The remaining Grignard reagent was slowly added while maintaining the pot temperature between 50° C. and 70° C. After the addition was complete, the reaction mixture was stirred at 70° C. for one hour. During this time, the green solids dissolved and the reaction mixture formed two liquid phases. After this time, the reaction was cooled and then quenched by slowly adding 80 mL of deionized water. The quenched reaction mixture was then poured into six liters of water. The organic phase was separated and the solvent removed in vacuo. The resulting crude product was then dissolved in warm hexane and filtered. The filtrate was washed with hexane (2×100 mL). The hexane portions were combined and solvent removed producing 242 grams (69.8 percent) of a viscous amber oil.

(B) 2,6-di-t-butyl-4-(1-trimethylsilyloxy-3-phenylpropyl) phenol

To a nitrogen-purged 250 mL three-neck round-bottom flask were added 141 grams (0.41 mole) of the 2,6-di-t-butyl-4-(1-hydroxy-3-phenylpropyl)phenol produced in step (A) of this example, 100 mL of toluene, and 54.3 grams (0.50 mole) of trimethylchlorosilane. The addition of the chlorosilane produced a several degree exotherm. The mixture was allowed to stir overnight at ambient temperature. After this time, the reaction mixture was washed with water (3×200 mL), dried with sodium sulfate, and filtered. Removal of the hexane gave 148.9 grams of desired product (87.1 percent).

(C) 2,6-di-t-butyl-4-(1-morpholino-3-phenylpropyl)phenol

To a nitrogen-purged, 250 mL, three-neck, round-bottom flask were added the 148.9 grams of the 2,6-di-t-butyl-4-(1- trimethylsilyloxy-3-phenylpropyl)phenol produced in step (B) of this example, 67 grams of hexane, and 45.8 grams (0.53 mole) of morpholine. The mixture was stirred overnight at ambient temperature. After this time, the solvent was removed and the solids recrystallized from a solution of 5 percent toluene in hexane to give pure 2,6-di-t-butyl-4-(1-morpholino-3-phenylpropyl)phenol as a white crystalline solid.

In view of the many changes and modifications that can be made without departing from principles underlying the invention, reference should be made to the appended claims for an understanding of the scope of the protection to be afforded the invention.

What is claimed is:

1. A method for the stabilization of (meth)acryloxysilanes during their production, storage, or both comprising adding thereto a compound of the structure

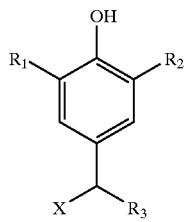

wherein
$R_1$, $R_2$, and $R_3$ are organic radicals of $C_1$ to $C_{20}$, such that the combination of the three contain at least twelve carbon atoms and $R_3$ is bound to the methylene carbon atom between X and the aromatic ring by at least one saturated carbon atom, allowing it to be easily separated from the polymerizable monomer by distillation; $R_1$ and $R_2$ have sufficient steric bulk to protect the phenol from reacting with an alkoxy group or halogen bound to silicon; and
X is a neutral heteroatomic radical of oxygen, nitrogen, or phosphorus.

2. The method of claim 1 wherein the compound is selected from the group consisting of
2,6-di-tert-butyl-4-(1-dimethylamino-3-phenylpropyl) phenol,
2,6-di-tert-butyl-4-(1-morpholino-3-phenylpropyl)phenol,
2,6-di-tert-butyl-4-(1-trimethylsilyloxy-3-phenylpropyl) phenol,
2,6-di-tert-butyl-4-(1-triphenylsilyloxy-3-phenylpropyl) phenol,
2,6-di-tert-butyl-4-(1-diphenylmethylsilyloxy-3-phenylpropyl)phenol,
2,6-di-tert-butyl-4-(1-tri-iso-propylsilyloxy-3-phenylpropyl)phenol,
2,6-di-tert-butyl-4-(1-diphenylphospho-3-phenylpropyl) phenol,
2,6-di-tert-butyl-4-(1-benzoyl-3-phenylpropyl)phenol,
2,6-di-tert-butyl-4-(1-dimethylaminotridecyl)phenol,
2,6-di-tert-butyl-4-(1-morpholinotridecyl)phenol,
2,6-di-tert-butyl-4-(1-trimethylsilyloxytridecyl)phenol,
2,6-di-tert-butyl-4-(1-diphenylphosphotridecyl)phenol,
2,6-di-tert-butyl-4-(1-benzoyltridecyl)phenol,
2,6-di-t-butyl-4-(1-benzoylpentyl)phenol,
2,6-di-t-butyl-4-(morpholinopentyl)phenol,
2,6-di-t-butyl-4-(1-dimethylaminopentyl)phenol, and
2,6-di-isooctyl-4-(1-dimethylamino-3-phenylpropyl) phenol.

3. The method of claim 1 further comprising the step of adding at least one additional inhibitor selected from the group consisting of inhibitors containing phenolic, amino, quinone, or nitroxide functionality.

4. The method of claim 1 wherein the (meth) acryloxysilane is of the structural formula $$CH_2=C(R)-CO_2-(R'O)_a(R'')_b-SiY,$$

wherein:
R is hydrogen or methyl;
R' is alkylene of two to four carbon atoms;
R" is alkylene;
Y is halide, alkoxy, alkoxy-substituted alkoxy or alkyl;
a is zero to ten;
b is at least one; and
a+b is a number from one to eleven.

5. The method of claim 4 wherein the (meth) acryloxysilane is selected from the group consisting of
3-acryloxypropyltrimethoxysilane,
3-acryloxypropyltriethoxysilane,
3-acryloxypropylmethyldimethoxysilane,
3-acryloxypropylmethyldiethoxysilane,
3-acryloxypropyldimethylmethoxysilane,
3-acryloxypropyldimethylethoxysilane,
3-methacryloxypropyltrimethoxysilane,
3-methacryloxyisobutyltrimethoxysilane,
3-methacryloxypropylmethyldimethoxysilane,
3-methacryloxypropylmethyldiethoxysilane,
3-methacryloxypropyldimethylmethoxysilane,
3-methacryloxypropyldimethylethoxysilane,
3-methacryloxyisobutylmethyldimethoxysilane,
3-methacryloxypropyltriethoxysilane,
3-acryloxypropyltrichlorosilane,
3-methacryloxypropyltrimethylsilane,
3-methacryloxypropyltrichlorosilane,
3-methacryloxyisobutyltrichlorosilane, and
3-methacryloxypropyl[tris(beta-methoxyethoxy)]silane.

6. The method of claim 5 wherein the (meth) acryloxysilane is 3-methacryloxypropyltrimethoxysilane.

* * * * *